United States Patent [19]

Shih

[11] 4,341,705
[45] Jul. 27, 1982

[54] THIENAMYCIN DERIVATIVES

[75] Inventor: David H. Shih, Manalapan, N.J.

[73] Assignee: Merck & Co., Inc., Rahway, N.J.

[21] Appl. No.: 195,993

[22] Filed: Oct. 10, 1980

[51] Int. Cl.³ .......................................... C07D 487/04
[52] U.S. Cl. ............................................ 260/245.2 T
[58] Field of Search ................................ 260/245.2 T

[56] References Cited

FOREIGN PATENT DOCUMENTS 2564 6/1979 European Pat. Off. .
8888 3/1980 European Pat. Off. .
7702183 9/1977 Netherlands .

OTHER PUBLICATIONS

Derwent Abstract of DT 2652676, pub. Nov. 21, 1975 and DT 2652674, pub. Nov. 21, 1975, and DT 2652676, pub. Nov. 19, 1976 and DT 2652680, pub. Nov. 19, 1976.

Primary Examiner—John M. Ford
Attorney, Agent, or Firm—James A. Arno; Hesna J. Pfeiffer

[57] ABSTRACT

Disclosed is a process for the total synthesis of thienamycin from descysteaminylthinamycin 1

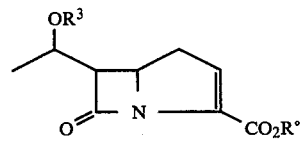

via thienamycin sulfoxide 4:

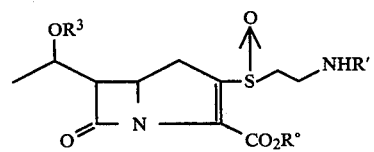

$R^3$, $R°$, $R'$ are blocking groups.

1 Claim, No Drawings

THIENAMYCIN DERIVATIVES

BACKGROUND OF THE INVENTION

This invention relates to the total synthesis of the known antibiotic thienamycin (I).

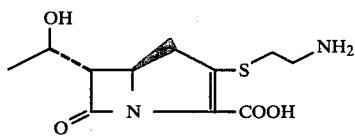
   I

Starting from descysteaminylthienamycin $\underset{\sim}{1}$, the synthesis proceeds via the reduction of thienamycin sulfoxide $\underset{\sim}{4}$.

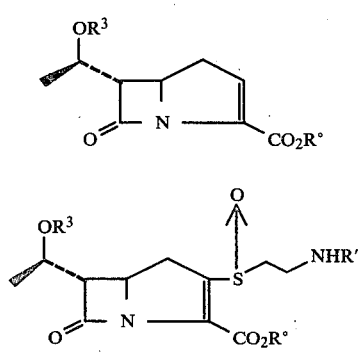

$R^3$, $R'$ and $R°$ are conventional, readily removable protecting groups which are defined below. The details of the total synthesis are given below.

DETAILED DESCRIPTION OF THE INVENTION

The process of the present invention may conveniently be summarized by the following reaction diagram:

DIAGRAM I

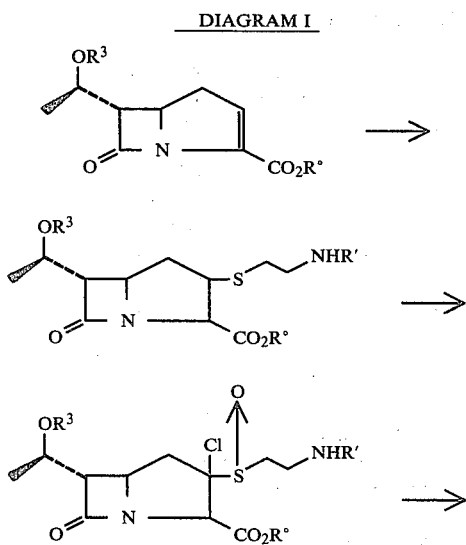

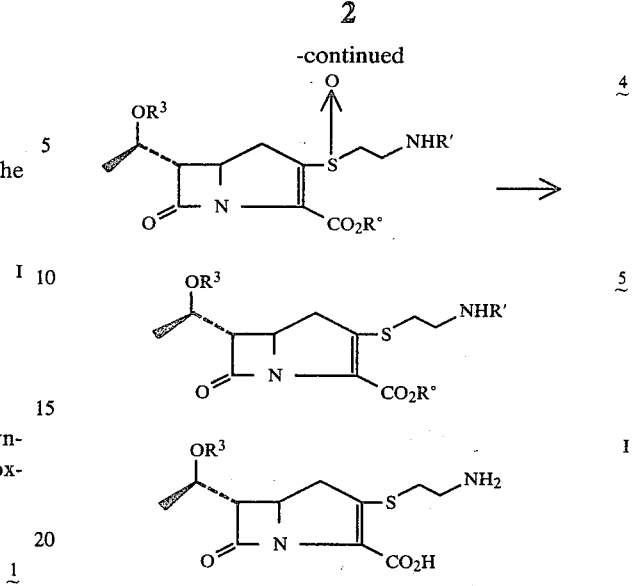

In words relative to diagram I, starting material, descysteaminylthienamycin $\underset{\sim}{1}$, is treated with one equivalent of N-protected aminoethanethiol, $HSCH_2CH_2NHR'$ wherein $R'$ is a readily removable protecting group such as p-nitrobenzyloxycarbonyl, o-nitrobenzyloxycarbonyl, or the like in the presence of a base such as sodium hydrogen carbonate, potassium carbonate, triethylamine, or the like in a solvent such as DMF, THF or the like at a temperature of from 0° C. to 60° C. for from 0.5 hr. to 6 hrs. Isomers of compound $\underset{\sim}{2}$ are conveniently separated by chromatography. However, the separation of isomers is not required in this synthesis. The oxidation of $\underset{\sim}{2} \rightarrow \underset{\sim}{3}$ is accomplished by treating $\underset{\sim}{3}$ with iodobenzene dichloride in a solvent such as methylene chloride, chloroform, carbon tetrachloride or the like at a temperature of from 0° C. to 60° C. for from 10 min. to 2 hrs. Dehydrochlorination of $\underset{\sim}{3}$ with a strong base such as 1,5-diazabicyclo[5.4.0]-undec-5-ene (DBU), 1,5-diazabicyclo[3.4.0]non-5-ene (DBN) or the like in a solvent such as ethyl acetate, acetone, THF and DMF, at a temperature of from 0° to 60° C. for from 1 min. to 3 hrs. Reduction (de-oxygenation) of thienamycin sulfoxide $\underset{\sim}{4} \rightarrow \underset{\sim}{5}$ is accomplished by treating $\underset{\sim}{4}$ with a reducing agent such as 2-phenoxy-1,3,2-benzodioxaphosphole, 2-chloro-1,3,2-benzodioxaphosphole, triphenyl phosphite, dichloroborane, iron pentacarbonyl, tin (II) chloride, diphosphorous tetraiodide, or the like.

The final deblocking step $\underset{\sim}{5} \rightarrow I$ is achieved by conventional procedures such as hydrolysis or hydrogenation. Typically $\underset{\sim}{5}$ in a solvent such as dioxane-water-ethanol, tetrahydrofuran-aqueous dipotassium hydrogen phosphate-isopropanol or the like is treated under a hydrogen pressure of from 1 4 atmospheres in the presence of a hydrogenation catalyst such as palladium on charcoal, palladium hydroxide, or the like at a temperature of from 0° to 60° C. for from 0.5 to 4 hrs. to provide I.

PREPARATION OF STARTING MATERIAL $\underset{\sim}{1}$

With respect to starting material $\underset{\sim}{1}$, its preparation is summarized by diagram II.

DIAGRAM II

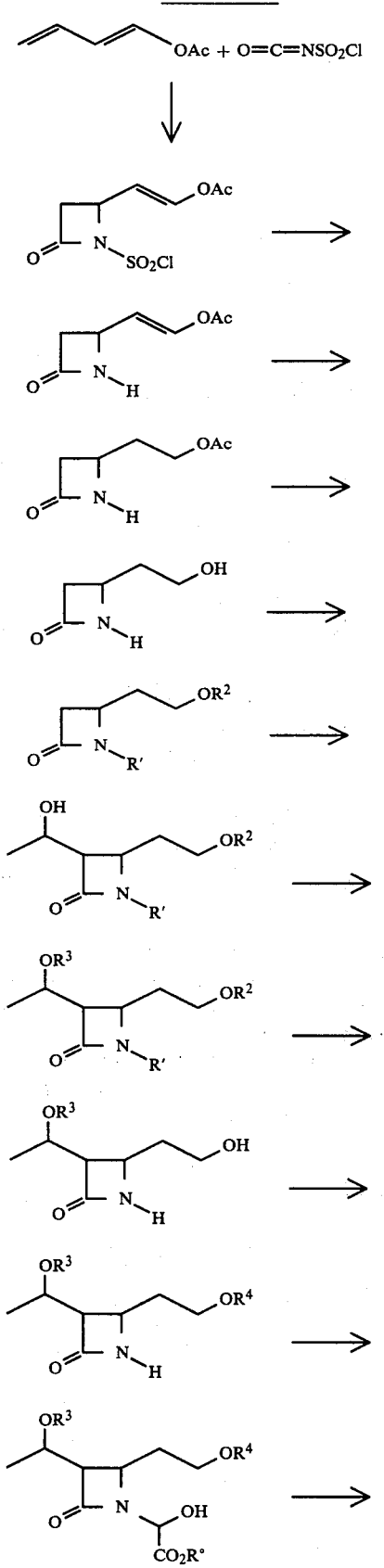

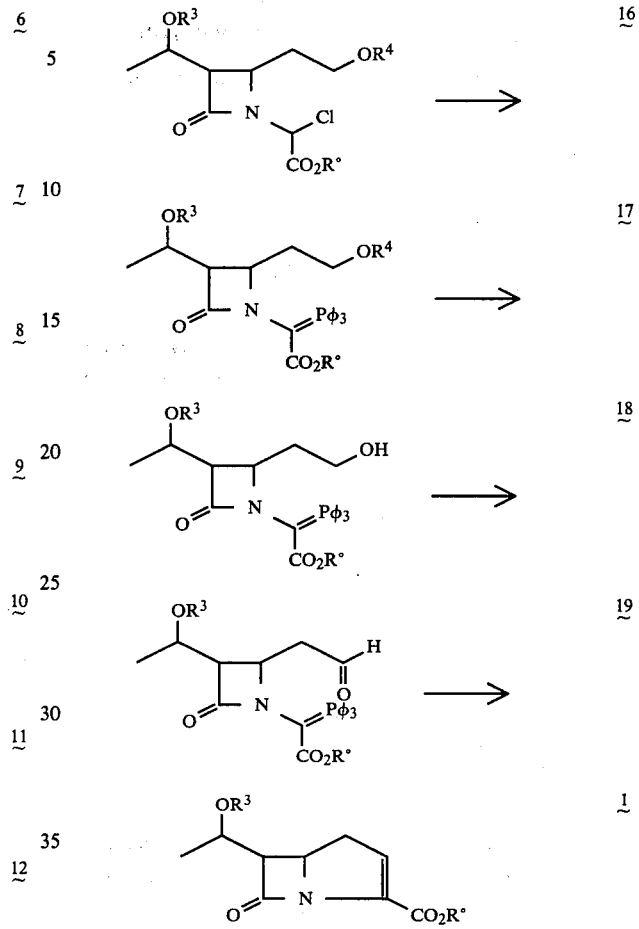

In words relative to the above diagram, the 4-(2-acetoxyl vinyl)azetidin-2-one, 8 is prepared by reacting an oxybutadiene, 6, with chlorosulfonylisocyanate. The reaction is conducted without solvent or may be run in solvent such as diethyl ether, ethyl acetate, chloroform, methylene chloride, or the like at a temperature of from −78° C. to 25° C. for from a few minutes to 1 hour to provide 7. Intermediate species 7 is converted to the sulfinamide by reduction which is then hydrolyzed to 8 at pH 6-8. Typically the reaction solution comprising 7 is contacted (5-30 minutes) with an aqueous solution (at 0°-25° C.) of a reducing agent such as sodium sulfite, thiophenol, or the like, at pH 6-8 to provide 8.

The reduction 8→9 is preferably achieved by hydrogenation in a solvent such as ethyl acetate, ether, dioxane, tetrahydrofuran (THF), ethanol or the like at 0° to 25° C. for from 5 minutes to 2 hours under 1 to 10 atmospheres of hydrogen in the presence of a hydrogenation catalyst such as a platinum metal or oxide thereof such as 10% Pd/C or the like.

The de-blocking reaction 9→10 is accomplished by alcoholysis wherein the solvent is a lower alkanol such as methanol, ethanol or the like in the presence of the corresponding alkali metal alkoxide, such as sodium methoxide. Typically, the reaction is conducted for from 5 minutes to 1 hour at a temperature of from −10° to 25° C.

Blocking groups R' and $R^2$ are established (10→11) to provide a suitably protected species for alkylation ($\underline{11} \rightarrow \underline{12}$). There is no criticality in the choice of blocking groups, provided only that they do not interfere with the intended alkylation. R' may be hydrogen, a triorganosilyl group such as trimethylsilyl, t-butyldimethylsilyl or the like, or a cyclic ether such as 2-tetrahydropyranyl; $R^2$ may also be a cyclic ether such as 2-tetrahydropyranyl or t-butyldimethylsilyl; alternatively R' and $R^2$ may be joined together to form protected species such as:

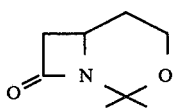

$\underline{11}a$

For example, species such as $\underline{11}a$ are conveniently prepared by treating $\underline{10}$ with 2,2-dimethoxypropane in the presence of a catalyst such as boron trifluoride etherate, toluene sulphonic acid, or the like in a solvent such as methylene chloride, ether, chloroform, dioxane or the like at a temperature of from $-10°$ C. to $35°$ C. for from a few minutes to 1 hour.

The alkylation ($\underline{11} \rightarrow \underline{12}$) is preferably conducted by treating $\underline{11}$ with a strong base such as lithium diisopropylamide, sodium amide, potassium hydride or the like in a solvent such as THF, glyme, ether, dimethylformamide (DMF), dimethylsulfoxide (DMSO) or the like at a temperature of from $-78°$ C. to $0°$ C. The resulting anion is then treated with excess acetaldehyde to provide $\underline{12}$.

The reaction $\underline{12} \rightarrow \underline{12}a$ establishes the blocking group $R^3$ and is typically accomplished by treating $\underline{12}$ with a base such as an alkali metal hydroxide, lithium diisopropyl amide, 4-dimethylaminopyridine, or n-butyllithium in a solvent such as ether, THF, dioxane, DMF, DMSO or the like, followed by treatment with an acyl halide of choice such as an alkanoyl, aralkanoyl or nuclear substituted aralkanoyl, or alkyl, aryl or aralkyl, substituted aralkyl or substituted aryl haloformate such as p-nitrobenzylchloroformate or the like at a temperature of from $-78°$ C. to $25°$ C. for from 1-24 hours.

The de-blocking reaction $\underline{12}a \rightarrow \underline{13}$ is typically conducted by acid hydrolysis such as aqueous acetic acid at a temperature of from $25°$ C. to $75°$ C. for from 5 minutes to 3 hours.

Selective protection of alcohol group of $\underline{13}$ ($\underline{13} \rightarrow \underline{14}$) is achieved by treating $\underline{13}$ with t-butyldimethyl chlorosilane in DMF in the presence of imidazole as base.

The azetidinone ($\underline{14}$) is reacted with a glyoxalate ester such as benzyl glyoxalate to form the corresponding 1-(benzyloxycarbonylhydroxymethyl)azetidinone ($\underline{15}$). The reaction $\underline{14} \rightarrow \underline{15}$ is conveniently carried out in a solvent such as benzene, toluene, xylene and the like at a temperature of from about $25°$ C. to reflux for from 2 to 10 hours. There is no criticality as to the precise identity of the solvent, provided only that it adequately solubilizes the reactants and be inert or substantially inert to the desired course of reaction. The halogenation reaction $\underline{15} \rightarrow \underline{16}$ may be conducted by any of a variety of well-known halogenation means. Suitable reagents include: $SOCl_2$, $POCl_3$, oxalyl chloride and the like. A preferred means of chlorination involves treating $\underline{15}$ in a solvent such as tetrahydrofuran (THF), ether, $CH_2Cl_2$ and the like with thionylchloride in the presence of 1 to 2 equivalents (relative to the thionylchloride) of a base such as pyridine, triethylamine, quinoline and the like. Typically, the reaction is conducted at a temperature of from $-30°$ to $25°$ C. for from 0.5 to 1 hour. The resulting 1-(benzoyloxycarbonylchloromethyl)-azetidinone species, $\underline{16}$, is isolated, if desired, by conventional procedures for later reaction $\underline{16} \rightarrow \underline{17}$. The intermediate $\underline{17}$ is prepared from $\underline{16}$ by treating $\underline{16}$ in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2-cyanoethyl)phosphine or the like. Typically the reaction is conducted under a nitrogen atmosphere at a temperature of from $-20°$ to $25°$ C., for from 0.5 to 2 hours. The reaction $\underline{17} \rightarrow \underline{18}$ is conducted at a temperature of from $0°$ to $25°$ C., for from 0.5 to 2 hours or is by an acid hydrolysis by treating $\underline{17}$ (R=triorganosilyl) with HCl in THF, DMF, or the like at $25°$ C. for 1 to 15 minutes. The ring closure reaction $\underline{18} \rightarrow \underline{1}$ proceeds via the oxo intermediate $\underline{19}$ and is achieved by treating $\underline{18}$ with an equivalent of an oxidizing system such as 1:1 mixture of dimethylsulfoxide (DMSO) and acetic anhydride ($Ac_2O$); other oxidizing systems include cyclohexylcarbodiimide in DMSO, $CrO_3 \cdot 2$(pyridine) in $CH_2Cl_2$, and pyridinum chlorochromate in $CH_2Cl_2$ for example. Typicallly, the closure step $\underline{19} \rightarrow \underline{1}$ is conducted at a temperature of from about $0°$ to $100°$ C. for from 0.25 to 24 hours in the oxidative system (DMSO/$Ac_2O$) described above or by heating from $100°-160°$ C. (after isolation of the oxo compound $\underline{6}$) in a solvent such as benzene, toluene, dioxane, xylene, or DMF.

The glyoxalate esters used to react with $\underline{14}$ can be prepared by oxidation of the corresponding tartaric acid diesters with oxidants such as periodic acid or lead tetracetate in a solvent such as THF, benzene, or methylene chloride at $-20°$ to $25°$ for $\frac{1}{2}$ to 4 hours. The tartarate esters are prepared from dilithio tartarate or disodio tartarate by reaction with $R°X$ wherein X is chloro, bromo or iodo and $R°$ is as defined above in a solvent such as DMF or DMSO at $25°$ to $70°$ C. for from 4 to 48 hrs. As noted above, $R°$ may be a pharmaceutically acceptable ester moiety. Such pharmaceutically acceptable esters and amides, however, may also be prepared from the free acid of I according to the procedure of co-pending U.S. patent application Ser. No. 861,314 filed Dec. 16, 1977, which is directed to the pharmaceutically acceptable ester and amides of thienamycin and their preparation. Accordingly, for its disclosure relative to such pharmaceutically acceptable forms and their means of preparation, the above-cited application is incorporated herein by reference.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

EXAMPLE 1

Preparation of 2 and 3

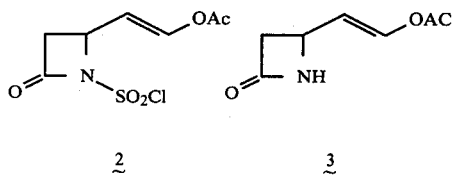

Chlorosulfonylisocyanate (CSI) (6.5 ml) is placed in a three-necked, 100-ml flask equipped with a thermometer, a magnetic stirring bar, a nitrogen inlet tube and a 25-ml pressure-equalized dropping funnel. The CSI is chilled to −50° C. and mixed with 12.5 ml ether through the dropping funnel. The etheral solution of CSI is allowed to warm up to −25° C.; to the solution is added dropwise 1-acetoxyl-1,3-butadiene (1) (5.9 ml in 12.5 ml ether) in 30 min. The mixture is then stirred for 20 min at −20±3° C. The white precipitate formed initially is redissolved at the end of the reaction.

In a 500-ml round bottom flask, a solution of 10 g sodium sulfite and 25 g potassium hydrogen phosphate in 100 ml water is prepared and is cooled in an ice bath. Ether (100 ml) and crushed ice (100 g) are added and the mixture is vigorously stirred in an ice bath. At the end of 20 minutes reaction time, the reaction mixture which contains 2 is transferred into the dropping funnel and added dropwise to the hydrolysis mixture in 5 minutes. The hydrolysis is allowed to continue for an additional 30 minutes at 3° C. The organic layer is separated and the aqueous is extracted with 50 ml ether. The organic layers are combined, dried over $Na_2SO_4$ and evaporated to give product 3 (2.3 g).

EXAMPLE 2

Preparation of 4

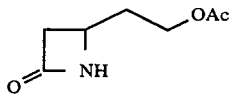

4-(2-acetoxyvinyl)azetidine-2-one (3) (6.5 g) is hydrogenated on a Parr shaker at r.t. under 40 psi hydrogen in the presence of 10% Pc/C (0.6 g) in 200 ml ethylacetate for 2 hr. The mixture is filtered from the catalyst and the filtrate is evaporated in vacuo to give the crude product. Purification of the crude product by high pressure liquid chromatograph (HPLC) (silical gel column 30% ethylacetate/$CH_2Cl_2$ solvent system) affords product 4 (6.04 g) after evaporation of solvent.

EXAMPLE 3

Preparation of 5

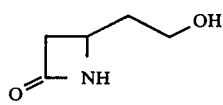

Under $N_2$ at 0°, a solution of 4-(1-2-acetoxyethyl)-2-azetidinone 4 (1.2 g) in 10 ml methanol is treated with sodium methoxide (57 mg). After stirring for 1 hr., the solution is neutralized with glacial acetic acid (65 mg). Removal of methanol in vacuo gives crude 4-(2-hydroxyethyl)-2-azetidinone (5). The product is purified by chromatography on silica gel eluting with ethyl acetate and gives 5.

EXAMPLE 4

Preparation of 6

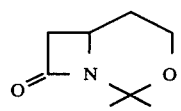

A solution of 4-(2-hydroxyethyl)-2-azetidinone (0.5 g) and 2,2-dimethoxypropane (0.48 g) in 10 ml anhydrous methylene chloride is treated with boron trifluoride (55 mg) at room temperature for 90 min. The mixture is washed with 5 ml saturated $NaHCO_3$. The organic layer is separated, dried over $Na_2SO_4$ and allowed to evaporate in vacuo to give 6.

EXAMPLE 5

Preparation of 7

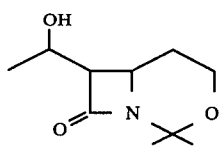

At −78° C., diisopropylamine (2.2 g) in 20 ml of anhydrous tetrahydrofuran is treated with n-butyllithium (1.6 M in n-hexane, 14 ml) for 5 min. To the solution is added 8-oxo 2,2-dimethyl-1-azabicyclo[4.2.-0]octane (6) (3.4 g) and the mixture is stirred for 10 min. The resulting lithium enolate is treated with acetaldehyde (1.68 ml). The mixture is stirred for 1 min. then is quenched with 24 ml saturated ammonium chloride at −78° C., then allowed to warm to room temperature (25° C.). The mixture is extracted with ethylacetate (2×100 ml). The organic layer is separated, dried over $Na_2SO_4$ and allowed to evaporate in vacuo to give 7.

The crude isomeric mixture of 7 is purified and separated by HPLC (silica gel) eluting with 50% ethylacetate/methylene chloride to give trans-7 and cis-7.

EXAMPLE 6

Preparation of 8

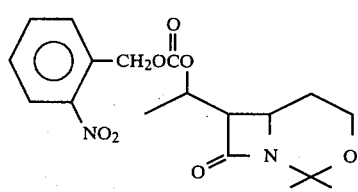

Under anhydrous conditions at 0° C. a solution of 7 (2.90 g) in 60 ml methylene chloride is treated with 4-dimethylaminopyridine (3.32 g) and o-nitrobenzylchloroformate (5.88 g). The mixture is allowed to warm to room temperature and stirred for 1 hr. The resulting mixture is washed with 0.1 N HCl, water, brine and water. The organic layer is separated, dried over Na₂SO₄ and allowed to evaporate in vacuo to give crude products. The crude products dissolved in 20 ml ether and chilled at −5° C. give the o-nitrobenzyl alcohol (0.5 g) which is separated by filtration. The mixture is purified and separated by HPLC (silica gel) eluting with 40% ethylacetate/cyclohexane to give 8.

EXAMPLE 7

Preparation of 9

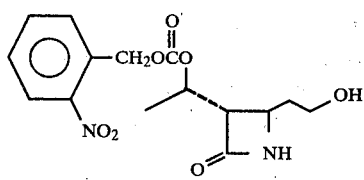

The bicyclic azetidinone 8 (2.1 g) is dissolved in 4 ml trifluoroacetic acid and 4 ml water at room temperature and the mixture is stirred for 10 minutes. The resulting homogeneous solution is slowly poured into a vigorously stirred saturated solution of potassium bicarbonate (30 ml) in a 200-ml beaker. The mixture is extracted with methylene chloride (200 ml). The organic layer is separated, dried over Na₂SO₄ and allowed to evaporate in vacuo to give crude product 9 which is purified by a silica gel column eluting with 40% ethylacetate/cyclohexane to afford 9.

EXAMPLE 8

Preparation of 10

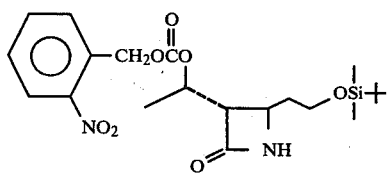

R-trans-1β

The starting material 9 (1.58 g) is treated with 5 equivalents of t-butyldimethylchlorosilane, 10 equivalents of imidazole in 5 ml anhydrous N,N-dimethylformamide (DMF) at room temperature for 3 hrs. The mixture is allowed to evaporate in vacuo to give crude product. Purification of the crude product by a silica gel eluting with 30% ethylacetate/cyclohexane gives 2.0 g of the product 10.

EXAMPLE 9

Preparation of 11

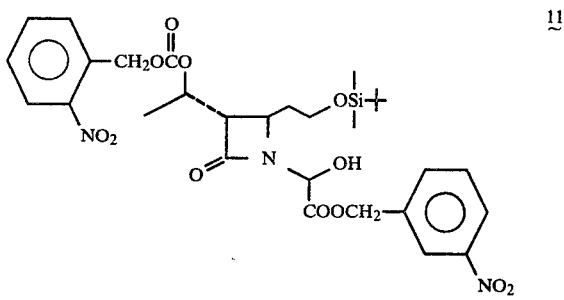

o-Nitrobenzyl-d-tartarate (1.8 g) is oxidized with periodic acid (0.97 g) in 18 ml of anhydrous tetrahydrofuran at 25° C. for 30 min. The mixture is filtered from solids and the filtrate is allowed to evaporate in vacuo to give o-nitrobenzylglyoxylate which is then taken up in 100 ml benzene and transferred into a 250-ml round bottom flask. To the solution is added 10 (2.0 g). The mixture is heated at reflux and water removed with a Dean-Stark trap packed with CaH₂ (1 g) for 6 hrs. The mixture is cooled, filtered, evaporated and chromatographed on silica gel eluting with 30% ethylacetate/cyclohexane to give 11.

EXAMPLE 10

Preparation of 12 and 13

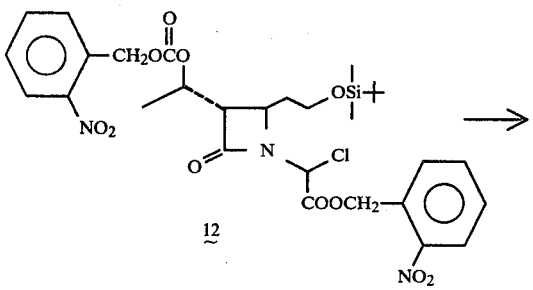

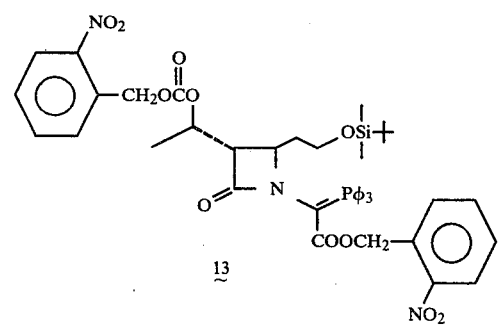

The azetidinone (11) (3.92 g) in 20 ml anhydrous tetrahydrofuran at −20° C. is treated with pyridine (0.42 ml) and thionyl chloride (0.37 ml). The mixture is allowed to warm to 25° C. with stirring, then filtered from solids. After removal of solvent in vacuo, product 12 is obtained. The chloride 12 is redissolved in 25 ml anhydrous DMF and treated with triphenylphosphine (1.1 g) with stirring at 25° C. for 1 hr. Solvent is removed in vacuo and the residue is dissolved in 100 ml methylene chloride and washed with 0.1 N pH 7.2 phosphate buffer 30 ml; chromatographic purification on silica gel, eluting with 40% ethylacetate/cyclohexane, gives product 13 (1.0 g).

EXAMPLE 11

Preparation of 14

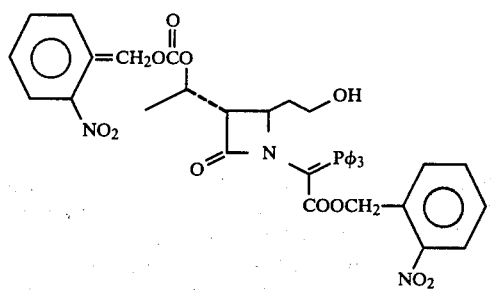

14

The azetidinone (13) (1.0 g) is dissolved in 10 ml tetrahydrofuran and is treated with conc. HCl (0.41 ml) at 25° C. for 10 min. The mixture is diluted with 200 ml methylene chloride then washed with 0.1 M $Na_2HPO_4$ (50 ml). The organic layer is separated, dried over $Na_2SO_4$ and evaporated in vacuo to give crude 14. Chromatographic purification of the crude product eluting with 30% ethylacetate/cyclohexane gives 14.

EXAMPLE 12

Preparation of 15

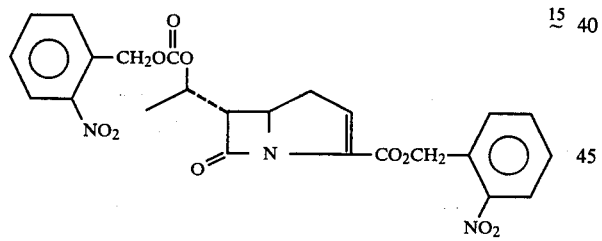

15

Azetidinone (14) (70 mg) is treated with 1 ml DMSO and 1 ml acetic anhydride at r.t. overnight. After solvents evaporated in vacuo the residue is chromatographed on TLC plate (silica gel GF, 500μ) eluting with 50% ethylacetate/cyclohexane to give 15.

EXAMPLE 13

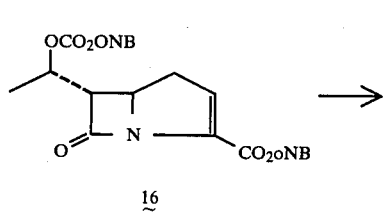

16

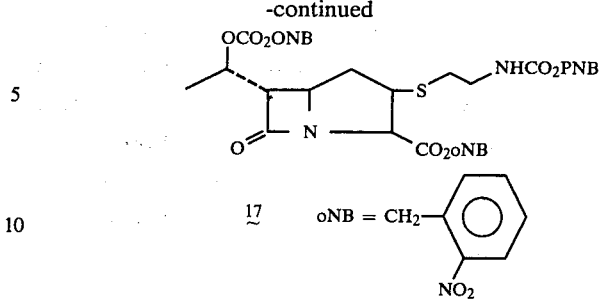

17    oNB = CH$_2$-C$_6$H$_4$-NO$_2$

The descysteaminylthienamycin ester 16 (372 mg) is dissolved in DMF (2 ml). To the solution is added N-p-nitrobenzyloxycarbonylaminoethanethiol (200 mg) and potassium carbonate (97 mg). The mixture is stirred at room temperature for 3 hrs., then is diluted with ethyl acetate, washed with water. The organic layer is separated, dried over $MgSO_4$ and concentrated in vacuo to give 17 (a mixture of isomers).

EXAMPLE 14

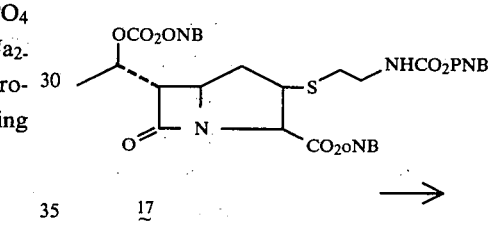

17

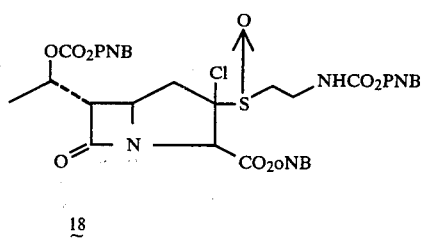

18

The azetidinone 17 (200 mg) is treated with iodobenzenedichloride (143 mg) in methylene chloride (10 ml) in the presence of pyridine (62 μl) and water (5 μl) at 0° C. for 1 hr. The mixture is evaporated in vacuo and the residue is chromatographed on silica gel plates eluting with ethylacetate to give 18.

EXAMPLE 15

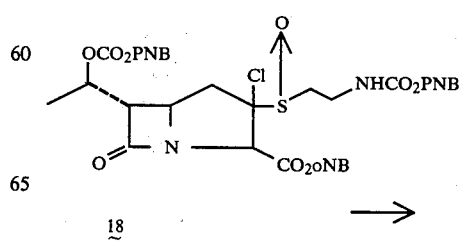

18

-continued

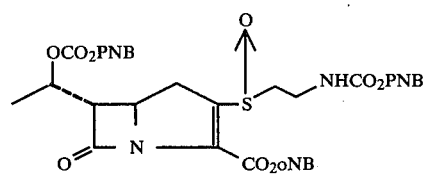

19

The chlorosulfoxide 18 (23 mg) in ethyl acetate (1.00 ml) is treated with 1.5-diazabicyclo [5.4.0]undec-5-ene (DBU) (4.2 μl) at room temperature for 2 hrs. The mixture is evaporated in vacuo and the residue is chromatographed on silica gel plates eluting with 50% ethylacetate/cyclohexane to give 19.

EXAMPLE 16

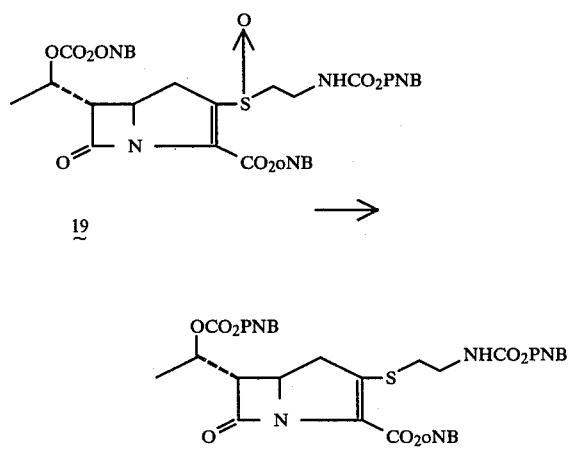

The thienamycin sulfoxide ester 19 (5 mg) in carbon tetrachloride (0.15 ml) is treated with 2-phenoxy-1,3,2-benzodioxaphosphole (1.5 mg) and iodine (0.5 mg) at reflux for 1 hr. The resultant mixture is cooled, diluted with ethyl acetate and washed once with water twice with 5% NaOH, then with aqueous hydrogen sulfite, and water. The organic layer is dried with MgSO4 and evaporated in vacuo to give 20.

EXAMPLE 17

Preparation of I

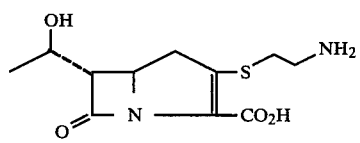

To 5.2 mg of 20 is added 0.60 ml dioxane, 0.05 ml ethanol, 0.35 ml deionized water and 0.01 ml of 1.0 M K2HPO4. To the resultant clear solution is added 5 mg of 10% Pd/C. The suspension is flushed with N2, then closed under 50 psi H2 atmosphere for 30–40 minutes. After centrifugation, the Pd/C is washed and centrifuged with 0.5 ml portions of deionized water. The combined centrifugates are extracted 5× with 2 ml portions ether. Residual ether is removed under vacuum and the aqueous solution is chromatographed on an XAD-2 column (20×140 mm) which is eluted with water to give the desired product I.

EXAMPLE 18

Preparation of Di-o-nitrobenzyltartarate

Tartaric acid (15.0 g, 0.1 mole) is dissolved in 40 ml. water and treated with lithium hydroxide (8.4 g, 0.2 mole). The resulting solution is evaporated to a small volume under reduced pressure and the residue is treated with p-dioxane. The resulting precipitate is filtered and dried under vacuum to give the di-lithium tartarate (17.7 g).

Di-lithium tartarate (9.46 g, 0.0585 mole) is suspended in 200 ml DMF and treated with o-nitrobenzyl chloride (20 g, 0.117 mole) and sodium iodide (17.5 g, 0.117 mole). The mixture is stirred under N2 for 2½ days at 65° C.

The solvent is removed under vacuum and the resulting paste is treated with water and sodium thiosulfate (5 g). The resulting solid is filtered and dried to give di-o-nitrobenzyltartarate (17.0 g, 0.040 mole, 69%, m.p. 128° C.).

n.m.r. (DMSO): 4.8 d(j=7, $\underline{H}$—C—OH), 5.23 d(j=7, H—C—$\underline{OH}$), 5.7 S((O—$\underline{CH_2}$C6H4—NO2); 7.73 and 8.2 m (aromatic H).

Similar treatment of the di-lithium salt with R'X (where X=Cl, Br or I) such as p-nitrobenzylbromide, benzylbromide, pivalyoxymethyl chloride gives the corresponding di-ester of tartaric acid such as di-p-nitrobenzyl tartarate, di-benzyl tartarate, dipivaloyloxymethyl tartarate. These can be used as equivalent alternates to di-o-nitrobenzyl tartarate in Example 2, below.

What is claimed is:

1. A compound having the formula:

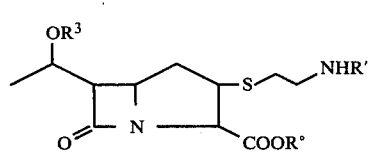

wherein: R' is selected from p-nitrobenzyloxycarbonyl, or o-nitrobenzyloxycarbonyl; R° is o-nitrobenzyl or p-nitrobenzyl; and R3 is o-nitrobenzyloxycarbonyl.

* * * * *